(12) United States Patent
Akitomo et al.

(10) Patent No.: US 11,572,580 B2
(45) Date of Patent: Feb. 7, 2023

(54) OLIGONUCLEOTIDE PRESERVATION METHOD

(71) Applicant: TAKARA BIO INC., Shiga (JP)

(72) Inventors: Miwa Akitomo, Kusatsu (JP); Takashi Uemori, Kusatsu (JP)

(73) Assignee: TAKARA BIO INC., Shiga (JP)

( * ) Notice: Subject to any disclaimer, the term of this patent is extended or adjusted under 35 U.S.C. 154(b) by 348 days.

(21) Appl. No.: 16/616,532

(22) PCT Filed: Jun. 6, 2018

(86) PCT No.: PCT/JP2018/021669
§ 371 (c)(1),
(2) Date: Nov. 25, 2019

(87) PCT Pub. No.: WO2018/225772
PCT Pub. Date: Dec. 13, 2018

(65) Prior Publication Data
US 2021/0164018 A1    Jun. 3, 2021

(30) Foreign Application Priority Data
Jun. 7, 2017 (JP) .............................. JP2017-112148

(51) Int. Cl.
*C12Q 1/6806* (2018.01)
*C07K 14/245* (2006.01)

(52) U.S. Cl.
CPC .......... *C12Q 1/6806* (2013.01); *C07K 14/245* (2013.01)

(58) Field of Classification Search
CPC ........................ C12Q 1/6806; C12Q 2522/101
See application file for complete search history.

(56) References Cited

U.S. PATENT DOCUMENTS

| | | | |
|---|---|---|---|
| 5,449,603 | A | 9/1995 | Nielson et al. |
| 5,605,824 | A | 2/1997 | Nielson et al. |
| 5,773,257 | A | 6/1998 | Nielson et al. |
| 6,127,155 | A | 10/2000 | Gelfand et al. |
| 2009/0011472 | A1 | 1/2009 | Nelson et al. |
| 2012/0129173 | A1* | 5/2012 | Piepenburg .......... C12Q 1/6806 435/6.11 |
| 2012/0219945 | A1 | 8/2012 | Lee |
| 2013/0323795 | A1 | 12/2013 | Duthie et al. |

FOREIGN PATENT DOCUMENTS

| | | |
|---|---|---|
| JP | 2008-516584 | 5/2008 |
| JP | 2009-273432 | 11/2009 |
| JP | 2011-512821 | 4/2011 |
| JP | 2014-513534 | 6/2014 |
| WO | 90/09444 | 8/1990 |
| WO | 2006/005074 | 1/2006 |
| WO | 2009/108949 | 9/2009 |
| WO | 2012/145725 | 10/2012 |

OTHER PUBLICATIONS

West, D.M. et al., Freezing complete polymerase chain reaction master mix reagents for routine molecular diagnostics, J. Vet. Diagn. Invest., vol. 18, pp. 580-582 (Year: 2006).*
Meyer, R.R. et al., A Temperature-Sensitive Single-stranded DNA-binding Protein from *Escherichia coli*, J. Biol. Chem., vol. 255, pp. 2897-2901 (Year: 1980).*
Falero, A. et al., Characterization of the single-stranded DNA binding protein pVVGJF of VGJF phage from Vibrio cholerae, Biochim. Biophys. Acta, vol. 1814, pp. 1107-1112 (Year: 2011).*
Extended European Search Report dated Feb. 10, 2021 in corresponding European Patent Application No. 18813443.1.
International Search Report dated Aug. 28, 2018 in International PCT Application No. PCT/JP2018/021669.
DNA Storage and Quality, Oxford Gene Technology website, https://www.ogt.com/resources/literature/403_dna_storage_and_quality, Aug. 22, 2011, 4 pages.
Brunstein, J., "Freeze-thaw cycles and nucleic acid stability: what's safe for your samples?", Medical Laboratory Observer, Sep. 2015, vol. 47, No. 9, pp. 44-45.
Kreader, C. A., "Relief of Amplification Inhibition in PCR with Bovine Serum Albumin or T4 Gene 32 Protein", Applied and Environmental Microbiology, Mar. 1996, vol. 62, No. 3, pp. 1102-1106.
Lorenz, T.C., "Polymerase Chain Reaction: Basic Protocol Plus Troubleshooting and Optimization Strategies", Journal of Visualized Experiments, May 22, 2012, vol. 63, e3998, pp. 1-14.
Schaudien, D. et al., "High Preservation of DNA Standards Diluted in 50% Glycerol", Diagnostic Molecular Pathology, Sep. 2007, vol. 16, No. 3, pp. 153-157.
Maffeo, C. et al., "Molecular mechanism of DNA association with single stranded DNA binding protein", Nucleic Acids Research, Oct. 20, 2017, vol. 45, No. 21, pp. 12125-12139.
Bochkarev, A. et al., "From RPA to BRCA2: lessons from single stranded DNA binding by the OB-fold", Current Opinion in Structural Biology, 2004, vol. 14, pp. 36-42.
English translation of the International Preliminary Report on Patentability dated Dec. 10, 2019 in International PCT Application No. PCT/JP2018/021669.
Office Action dated Mar. 15, 2022 in corresponding Japanese Patent Application No. 2019-523936 with English Machine Translation, 8 pages.
Office Action dated Nov. 24, 2022 in corresponding Chinese Patent Application No. 201880037834.6, with English translation, 18 pages.

* cited by examiner

*Primary Examiner* — Teresa E Strzelecka
(74) *Attorney, Agent, or Firm* — Wenderoth, Lind & Ponack, L.L.P.

(57) ABSTRACT

The present invention pertains to: an oligonucleotide preservation method; and a kit comprising an oligonucleotide. The present invention provides a method for stably preserving an oligonucleotide-containing solution by adding a nucleic acid-binding protein to said oligonucleotide-containing solution in advance.

15 Claims, 4 Drawing Sheets
Specification includes a Sequence Listing.

[Fig. 1]
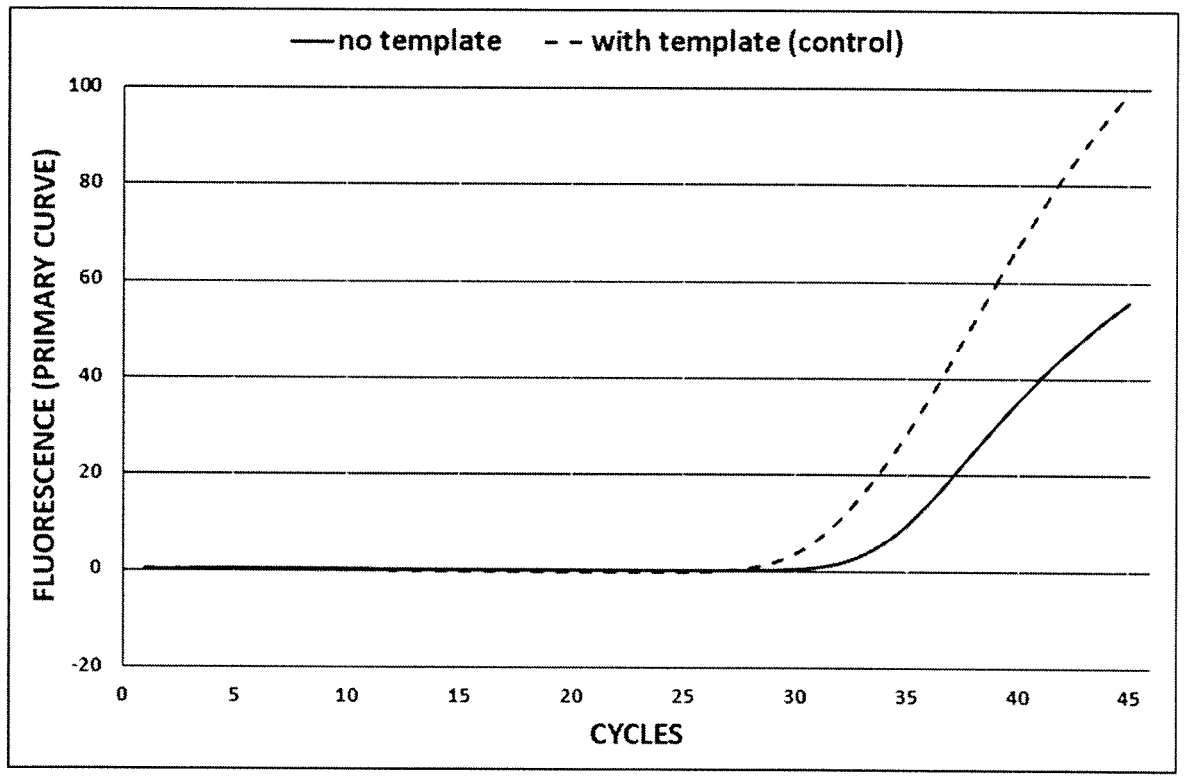
[Fig 2]
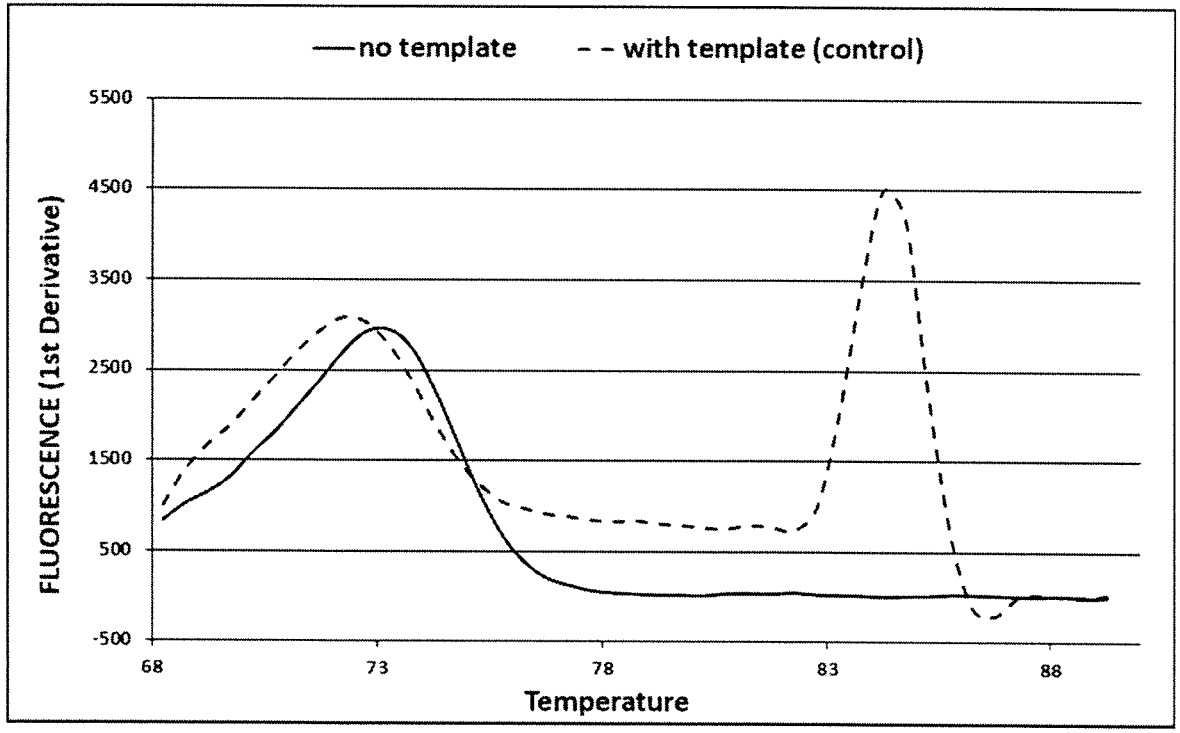

[Fig. 3]
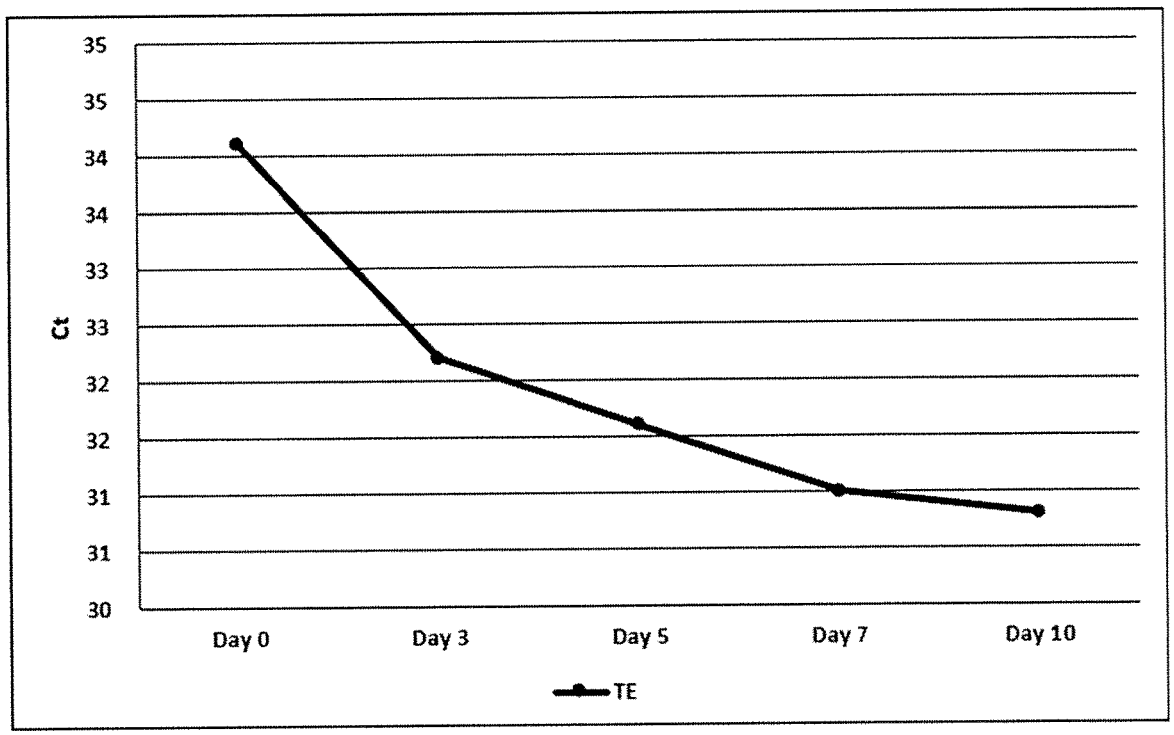
[Fig. 4]
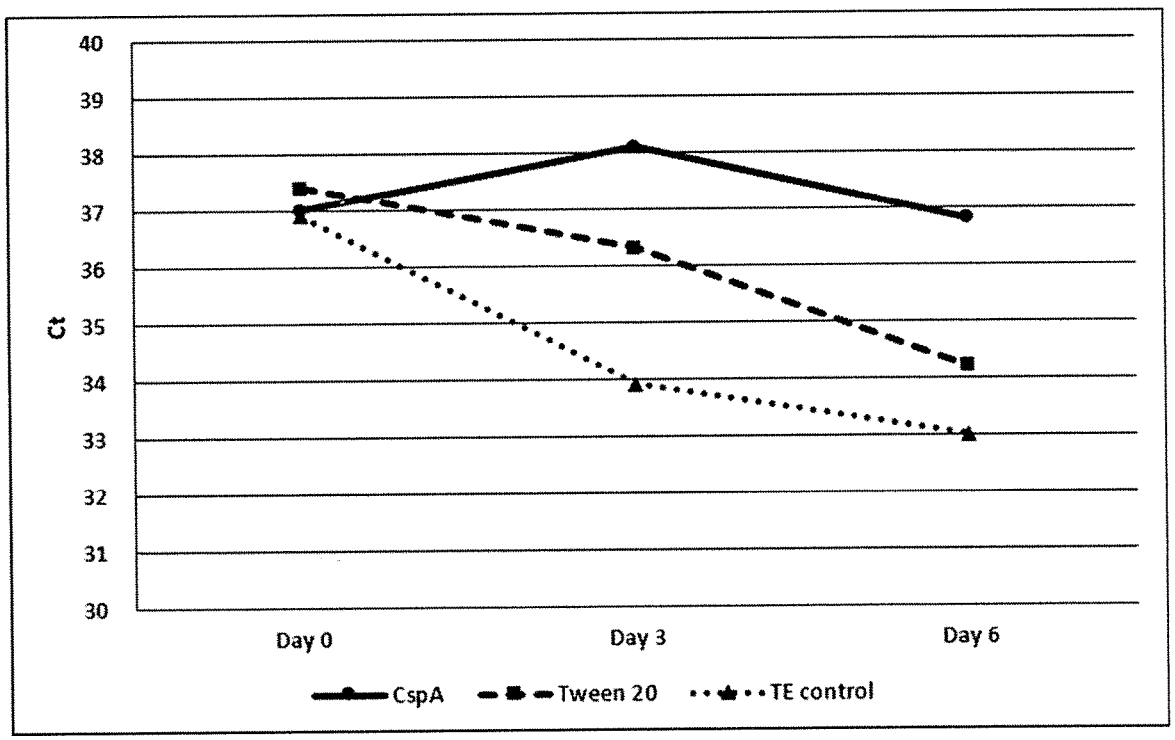

[Fig 5]
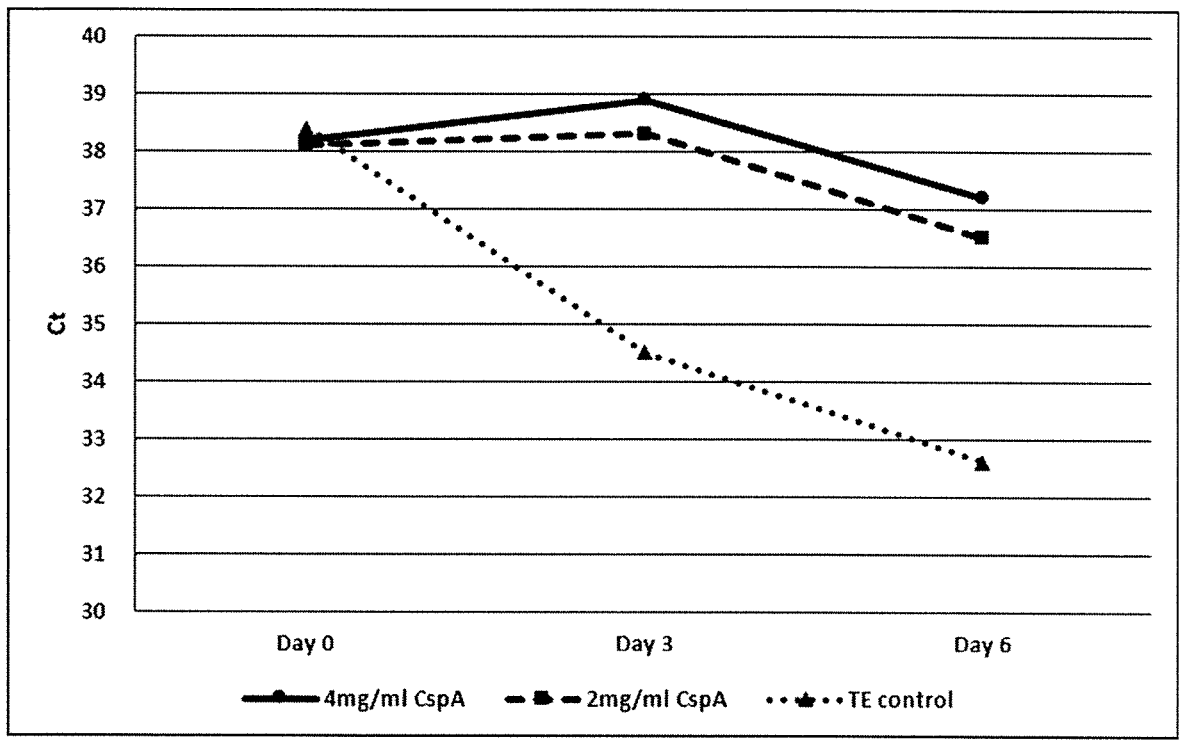
[Fig 6]
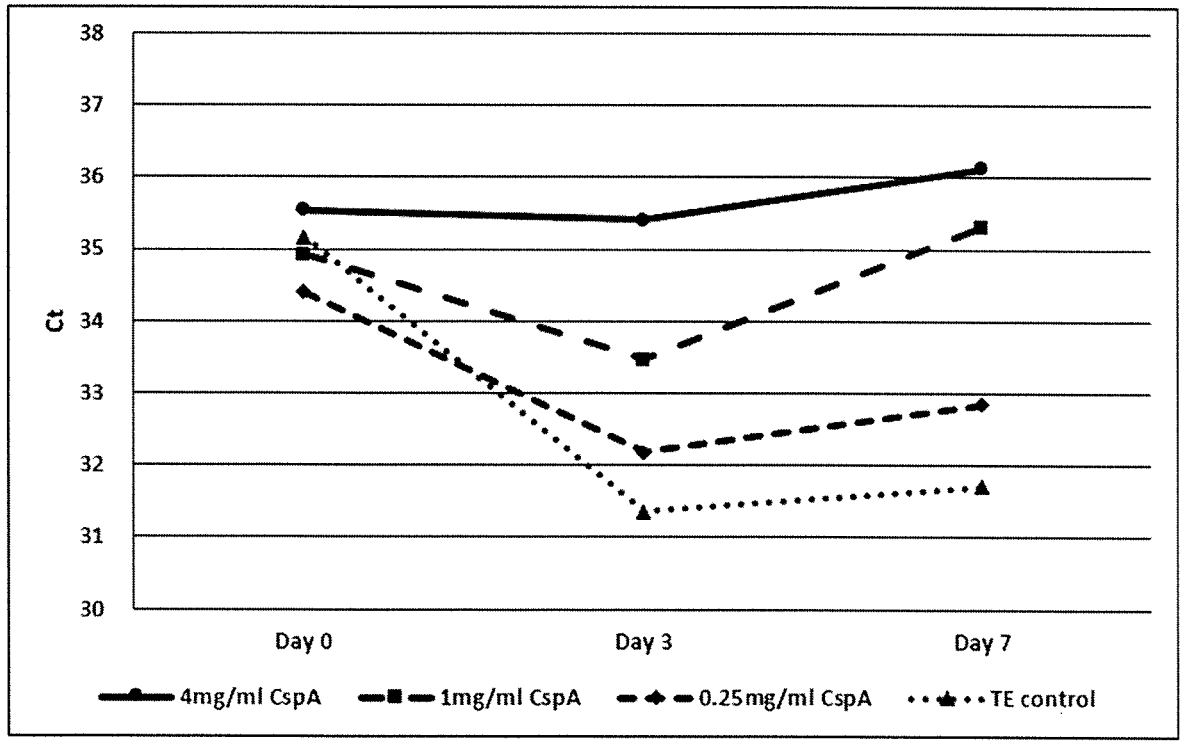

[Fig 7]
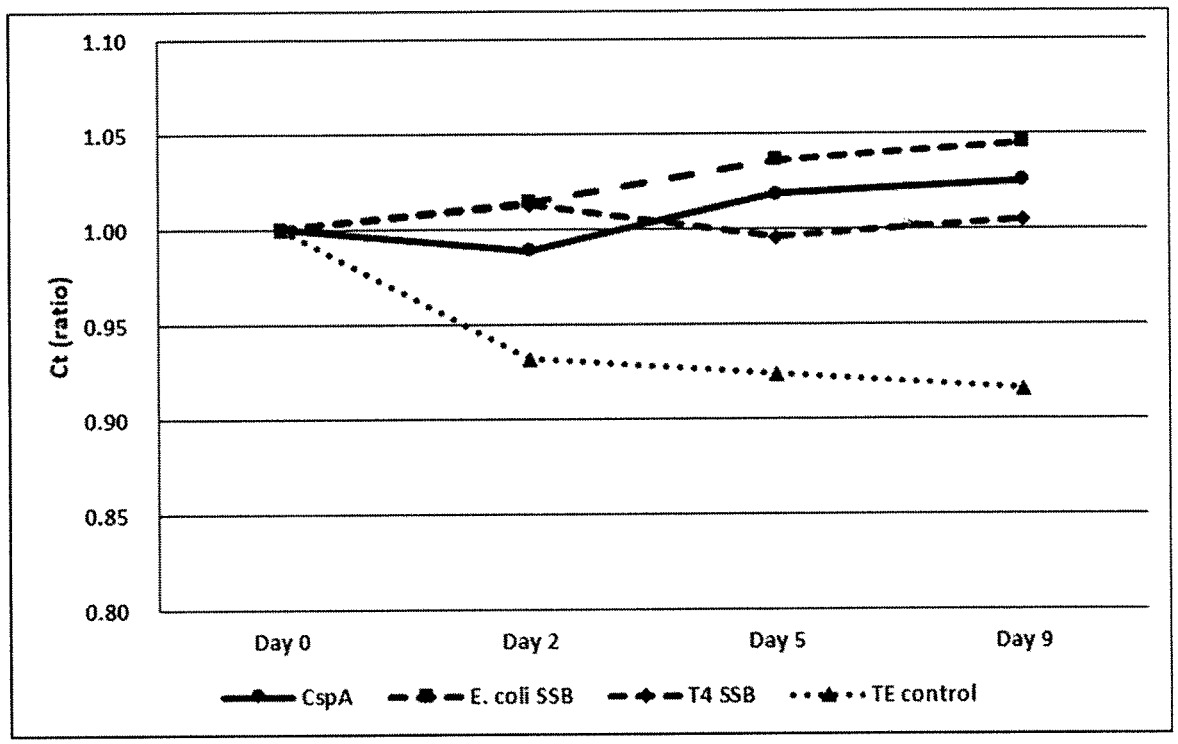
[Fig 8]
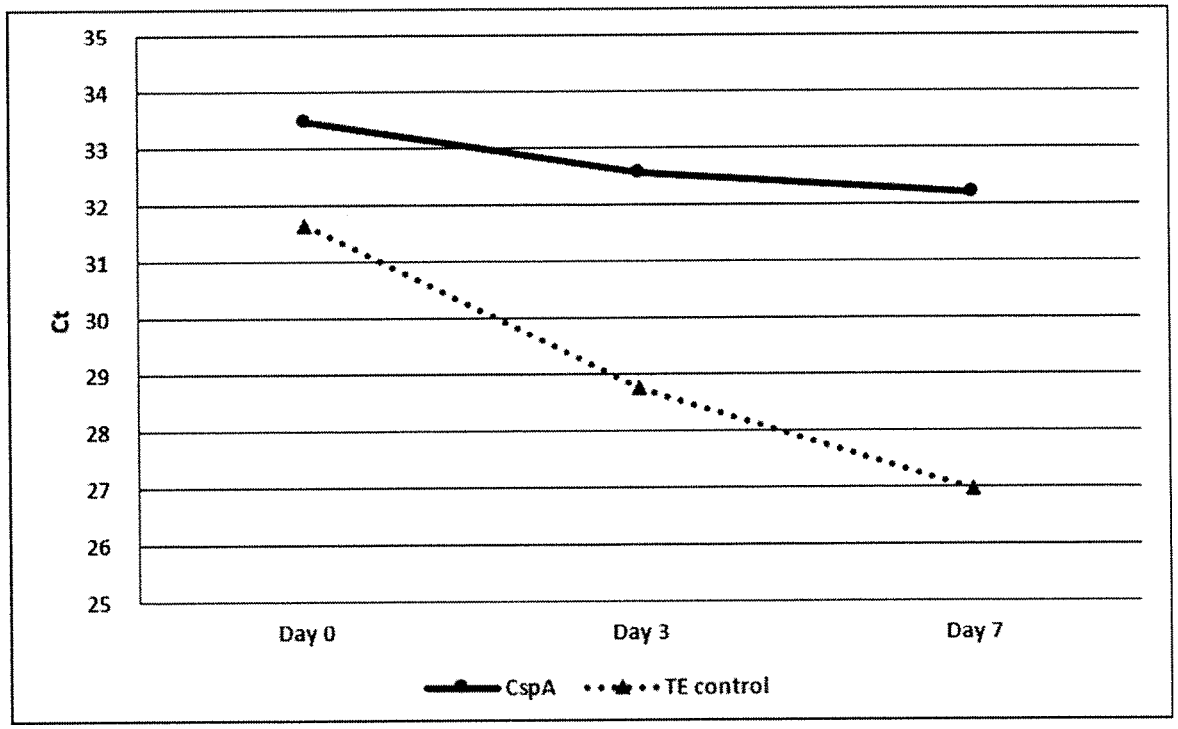

OLIGONUCLEOTIDE PRESERVATION METHOD

TECHNICAL FIELD

The present invention relates to an oligonucleotide storage method and a kit for amplifying a target nucleic acid.

BACKGROUND ART

DNA syntheses are used for various purposes in research. Among them, most DNA syntheses excluding chemical synthesis of single-stranded DNA are performed by enzymatic methods using DNA polymerase or reverse transcriptase. Polymerase chain reaction (hereinafter referred to as PCR), which can easily amplify a desired DNA fragment in vitro, is very useful and is an essential tool in the fields of biology, medicine, and agriculture, and other fields. In DNA amplification by PCR, high reaction specificity is often required. In order to reduce non-specific amplification, novel DNA polymerases have been developed and the composition of a reaction mixture (hereinafter referred to as a reaction solution) has been optimized. However, there is still a need for improved PCR amplification specificity.

Generally, in DNA amplification by PCR, a reaction solution contains ingredients such as a template nucleic acid, primers, deoxyribonucleotides, and an enzyme. In the case of detecting amplified DNA, the reaction solution may further contain a fluorescent dye or a probe. In order to realize a stable and accurate DNA synthesis reaction, it is important to appropriately store these ingredients until they are supplied to a reaction solution or PCR is started.

It is possible to store a primer or a probe as a solid or a solution (including a frozen solution). The solid has the merit that it can be stored at room temperature because of its stability, while it has the demerit that it must be dissolved to be used in a reaction solution. On the other hand, a primer or probe stored in a solution can be used immediately in a reaction solution. Furthermore, PCR can be performed rapidly by preparing and storing in advance a reaction solution containing all the ingredients necessary for PCR, such as primers, probes, deoxyribonucleotides, and enzymes. However, storage in a solution has the demerit of lacking stability. In other words, when a primer or probe is stored in a solution, the reactivity of PCR using the primer or probe tends to decrease. Although a decrease in the reactivity can be suppressed by storing the solution at a low temperature or a freezing temperature, a more effective storage method is required.

Various improvements have been made for the purpose of improving the reactivity and specificity of PCR. For example, a surfactant or a certain type of protein may be added to PCR. As the improvement of PCR, a technique of adding a nonionic surfactant is reported (Patent Literature 1). In addition, it is known that a protein having nucleic acid binding activity, for example, a protein that binds to a single-stranded nucleic acid suppresses non-specific nucleic acid synthesis in nucleic acid synthesis reaction such as PCR (Patent Literature 2). Examples of the protein that binds to a single-stranded nucleic acid include E. coli-derived SSB and T4 phage-derived SSB (also referred to as T4 gene 32 protein). Furthermore, a method for improving the reactivity of DNA synthesis reaction comprising adding a cold shock protein in preparation of a DNA synthesis reaction solution has been reported (Patent Literature 3).

The cold shock proteins are found from various microorganisms, and are believed to be involved in adaptation to shift of growing temperature to a low temperature. Among them, regarding CspA which is known as Major Cold Shock Protein, its gene was isolated from Escherichia coli and a recombinant was produced (Patent Literature 4). CspA has a property of binding to single-stranded DNA or single-stranded RNA.

As described above, it is known that a protein having a nucleic acid binding activity has a beneficial effect on DNA synthesis reaction. In the methods as described above, the protein is added to a reaction solution immediately before the start of synthesis reaction. However, the effect of the protein has never been studied regarding long-term storage of a solution containing a primer or probe.

CITATION LIST

Patent Literatures

Patent Literature 1: U.S. Pat. No. 6,127,155
Patent Literature 2: U.S. Pat. No. 5,773,257
Patent Literature 3: WO2009/108949
Patent Literature 4: WO90/09444

SUMMARY OF INVENTION

Problem to be Solved by the Invention

As described above, there is a problem that storage of a primer or probe in a solution state lacks stability. Furthermore, the present inventors have found a problem that even if a primer or probe is stored in a solution state at a low temperature or cryopreserved, it may lack stability (for example, Example 1). An object of the present invention is to provide a method for stably storing a solution containing an oligonucleotide such as a primer or probe.

Solutions to the Problems

As a result of diligent efforts to solve the above-mentioned problems, the present inventors have found that an oligonucleotide can be stably stored by adding a nucleic acid binding protein in advance to a solution containing the oligonucleotide. Thus the present invention was completed.

That is, the present invention relates to:

[1] A method for storing an oligonucleotide, the method comprising a step of storing a solution containing a nucleic acid binding protein and an oligonucleotide at a low temperature;

[2] The method according to [1], wherein the nucleic acid binding protein is a protein that binds to a single stranded nucleic acid;

[3] The method according to [2], wherein the protein that binds to a single-stranded nucleic acid is a protein selected from the group consisting of cold shock proteins and SSB;

[4] The method according to [2], wherein the protein that binds to a single-stranded nucleic acid is a protein selected from the group consisting of CspA, T4 phage-derived SSB, and E. coli-derived SSB;

[5] The method according to any one of [1] to [4], wherein the oligonucleotide is an oligodeoxyribonucleotide;

[6] The method according to any one of [1] to [5], comprising a step of freeze-storing the solution;

[7] A kit for amplifying a target nucleic acid, comprising a solution containing a nucleic acid binding protein and an oligonucleotide that hybridizes to the target nucleic acid;

[8] The kit according to [7], wherein the nucleic acid binding protein is a protein that binds to a single-stranded nucleic acid;

[9] The kit according to [8], wherein the protein that binds to a single-stranded nucleic acid is a protein selected from the group consisting of cold shock proteins and SSB;

[10] The kit according to [9], wherein the protein that binds to a single-stranded nucleic acid is a protein selected from the group consisting of CspA, T4 phage-derived SSB, and *E. coli*-derived SSB;

[11] The kit according to any one of [7] to [10], wherein the oligonucleotide is an oligodeoxyribonucleotide;

[12] The kit according to [11], wherein the oligodeoxyribonucleotide is a primer used for amplification of the target nucleic acid;

[13] The kit according to any one of [7] to [12], wherein the solution containing a nucleic acid binding protein and an oligonucleotide that hybridizes to the target nucleic acid is stored at a low temperature;

[14] The kit according to any one of [7] to [13], wherein the solution containing a nucleic acid binding protein and an oligonucleotide that hybridizes to the target nucleic acid is a frozen solution;

[15] The kit according to any one of [7] to [14], comprising a first solution containing a nucleic acid binding protein and an oligonucleotide that hybridizes to the target nucleic acid, and a second solution containing one or more elements selected from the group consisting of a DNA polymerase, a divalent metal ion, deoxyribonucleoside triphosphates, and a buffer ingredient;

[16] The kit according to any one of [7] to [14], wherein the solution containing a nucleic acid binding protein and an oligonucleotide that hybridizes to the target nucleic acid further contains a DNA polymerase, a divalent metal ion, deoxyribonucleoside triphosphate, and a buffer ingredient.

Effects of the Invention

The present invention provides a method for storing an oligonucleotide, which is useful for nucleic acid synthesis reaction. The present invention also provides a kit for amplifying a target nucleic acid.

BRIEF DESCRIPTION OF DRAWINGS

FIG. 1 is a graph showing an example of an amplification curve of PCR in Example 1.
FIG. 2 is a graph showing an example of a PCR melting curve in Example 1.
FIG. 3 is a graph showing Ct values in Example 1.
FIG. 4 is a graph showing Ct values in Example 2.
FIG. 5 is a graph showing Ct values in Example 3.
FIG. 6 is a graph showing Ct values in Example 4.
FIG. 7 is a graph showing Ct values in Example 5.
FIG. 8 is a graph showing Ct values in Example 6.

MODE FOR CARRYING OUT THE INVENTION

Definition

As used herein, the term "nucleic acid" (including "polynucleotide" and "oligonucleotide") means a linear polymer formed by linking nucleosides in a chain. Examples of the nucleic acid include a deoxyribonucleic acid, a ribonucleic acid, deoxyribonucleotides, ribonucleotides, and a polyamide nucleic acid. A natural nucleic acid, an artificial nucleic acid, as well as a modified nucleic acid and fragments thereof are also included in the "nucleic acid".

As used herein, the term "primer" refers to an oligonucleotide that functions as a starting point in nucleic acid synthesis reaction that occurs in the presence of a DNA or RNA template and a polymerization reagent (DNA polymerase, nucleoside triphosphate, etc.). The primer is preferably single stranded. However, a double-stranded primer can also function as described above. When a double stranded primer is used, it is desirable to convert it to its single stranded form prior to use in amplification reaction. The primer can be synthesized chemically or enzymatically using a well-known method or can be isolated from an organism.

As used herein, the term "probe" refers to an oligonucleotide for detecting or quantifying a target nucleic acid which can specifically hybridize with the target nucleic acid; The probe is preferably single-stranded. However, a double-stranded probe can also function as described above. When a double-stranded probe is used, it is desirable to convert it to its single stranded form prior to use in detection reaction. The probe can be synthesized chemically or enzymatically using a well-known method or can be isolated from an organism.

(1) "Oligonucleotide Storage Method" of the Present Invention

The oligonucleotide storage method of the present invention is characterized by comprising a step of storing a solution containing a nucleic acid binding protein and an oligonucleotide at a low temperature.

A step of preparing the solution containing a nucleic acid binding protein and an oligonucleotide (hereinafter referred to as "the solution of the present invention") is explained below.

<Oligonucleotide>

The oligonucleotide in the present invention usually includes a DNA (oligodeoxyribonucleotide) formed by linking deoxyribonucleotides having any base selected from the group consisting of adenine, guanine, cytosine and thymine and/or an RNA (oligoribonucleotide) formed by linking ribonucleotides having any base selected from the group consisting of adenine, guanine, cytosine and uracil, and a nucleic acid formed by linking natural nucleotides, such as a chimera of DNA and RNA. The oligonucleotide may be prepared by digesting a natural nucleic acid existing in nature with a restriction endonuclease or the like and then isolating the oligonucleotide from the digested product. Oligonucleotides artificially produced by enzymatic or chemical methods are also included in the oligonucleotide of the present invention.

The oligonucleotide used in the present invention further includes a non-natural nucleic acid. As used herein, "non-natural nucleic acid" refers to an artificially constructed nucleic acid analog having structure and/or property similar to that of a natural nucleic acid. Examples of the non-natural nucleic acid include a peptide nucleic acid (PNA: Peptide Nucleic Acid), a peptide nucleic acid having a phosphate group (PHONA), a nucleic acid containing a non-natural base (inosine, deazaguanosine, etc.), a cross-linked nucleic acid (BNA/LNA: Bridged Nucleic Acid/Locked Nucleic Acid), a morpholino nucleic acid, and the like. Oligonucleotides including chemically modified nucleic acids and nucleic acid analogs such as methylphosphonate DNA/RNA, phosphorothioate DNA/RNA, phosphoramidate DNA/RNA, and 2'-O-methyl DNA/RNA can be also used in the present invention. Furthermore, the oligonucleotide may be an oligonucleotide to which a fluorescent substance, a quenching substance, a dye, a hapten, biotin or the like is added.

In the present invention, the oligonucleotide may be a single-stranded oligonucleotide, a double-stranded oligonucleotide, or a mixture of these oligonucleotides. For example, the oligonucleotide may be an oligonucleotide that hybridizes to a target nucleic acid. Examples of the oligonucleotide that hybridizes to a target nucleic acid include an oligonucleotide that functions as a probe for detecting the target nucleic acid, and an oligonucleotide that functions as a primer in amplification of the target nucleic acid.

In the present invention, the length of the oligonucleotide is not particularly limited. When the oligonucleotide is single-stranded, the length is preferably 6 nucleotides or longer, more preferably 10 nucleotides or longer. When the oligonucleotide is an artificially synthesized single-stranded oligonucleotide, the length is preferably 100 nucleotides or shorter, more preferably 30 nucleotides or shorter, from the viewpoint of oligonucleotide synthesis. The oligonucleotide can be synthesized, for example, by a phosphoramidite method. The oligonucleotide may be synthesized by other methods such as a phosphotriester method, an H-phosphonate method, and a thiophosphonate method. The oligonucleotide may be also prepared by enzymatically or chemically cleaving a natural nucleic acid.

The number of types of oligonucleotides contained in the solution of the present invention is not particularly limited. For example, one or more, preferably two or more, more preferably three or more types of nucleic acids are contained in the solution of the present invention. When 2 or more types of oligonucleotides are used, a mixing ratio of the oligonucleotides is not limited. Examples of the 2 or more types of oligonucleotides include, but not limited to, a mixture of primer pairs having different nucleotide sequences used for multiplex nucleic acid amplification reaction. In addition to the mixture, the solution of the present invention may contain an oligonucleotide used as a probe for detecting a target nucleic acid.

The concentration of the oligonucleotide contained in the solution of the present invention is not particularly limited as long as the effect of the present invention can be achieved, and it can be appropriately determined considering the type of oligonucleotide, the type and concentration of the nucleic acid binding protein, the type and concentration of other ingredients, the storage temperature and the like. In the case of using a single-stranded oligonucleotide DNA(s) having chain length of 10 to 30 nucleotides, the total concentration is, for example, 0.1 to 100 µM, preferably 0.5 to 50 µM, more preferably 1 to 20 µM.

<Nucleic Acid Binding Protein>

The nucleic acid binding protein used in the present invention is not particularly limited as long as it is a protein capable of binding to a nucleic acid. The nucleic acid binding protein may be a protein isolated from the natural world or an artificially prepared recombinant protein. Preferably, the nucleic acid binding protein used in the present invention is a recombinant protein.

Examples of the nucleic acid binding protein used in the present invention include a protein that binds to a single-stranded nucleic acid. The protein that binds to a single-stranded nucleic acid may be any protein that can bind to a single-stranded nucleic acid, that is, a single-stranded DNA and/or a single-stranded RNA. Examples of the protein that binds to a single-stranded nucleic acid include, but not limited to, SSB (Single-Stranded Binding protein) and cold shock proteins.

Examples of the SSB used in the present invention include SSB derived from microorganisms including *E. coli*, Drosophila, Xenopus, and bacteriophages (T4 phage, T7 phage, etc.). Preferable examples thereof include SSB derived from *E. coli* and SSB derived from T4 phage. SSB has the property of binding to a single-stranded DNA. The SSB derived from T4 phage is also referred to as T4 gene 32 protein (T4gp32).

When the culture temperature of *E. coli* is lowered from 37° C. to 15° C., CspA is transiently expressed at a high level. *E. coli* is known to have 8 types of proteins CspB to CspI as homologues having amino acid sequence identity with CspA (J. Bacteriol., 1999, 181, 1603-1609). Furthermore, it is known that CspA homologues also exist in microorganisms such as *Bacillus subtilis* (CspB), *Bacillus caldoliticus* (CspB), *Thermotoga maritima* (CspB, CspL), and *Lactobacillus plantarum* (CspL). In the present invention, the "cold shock protein" means a protein having an amino acid sequence showing a sequence identity of preferably 80% or more, more preferably 90% or more, and still more preferably 95% or more with the amino acid sequence of *E. coli* CspA.

These cold shock proteins can be used in the present invention. Examples of the cold shock protein used in the present invention are preferably CspA, more preferably CspA derived from a Gram-negative bacterium, and still more preferably CspA from *E. coli*. CspA has the property of binding to a single-stranded DNA and a single-stranded RNA.

As described above, SSB derived from *E. coli* (GenBank Acc. No. NP 418483.1), SSB derived from T4 phage (GenBank Acc. No. NP 049854.1), and CspA derived from *E. coli* (GenBank Acc. No. NP 418012.1) can be used in the present invention. These proteins share homology regions in their amino acid sequences. That is, the partial amino acid sequence (VASEYLRKGSQV) of *E. coli*-derived SSB, the partial amino acid sequence (EGANNFVLKVKQV) of T4 phage-derived SSB, and the partial amino acid sequence (DGYKSLDEGQKV) of *E. coli*-derived CspA are homologous to each other. A nucleic acid-binding protein having an amino acid sequence showing a sequence identity of 70% or more, preferably 80% or more, more preferably 90% or more, and still more preferably 95% or more with any of the above-described partial amino acid sequences may produce the same effect as the protein having the partial amino acid sequence in the present invention, and therefore can be used in the present invention.

The number of types of nucleic acid binding proteins contained in the solution of the present invention is not particularly limited. For example, the solution of the present invention may contain one type of the nucleic acid binding protein, or may contain two or more types of the nucleic acid binding proteins. When two or more types of the nucleic acid binding proteins are used, a mixing ratio of them is not limited.

The concentration of the nucleic acid binding protein contained in the solution of the present invention is not particularly limited as long as the effect of the present invention can be achieved, and it can be appropriately determined considering the type and concentration of the oligonucleotide, the type of the nucleic acid binding protein, the types and concentrations of other ingredients, the storage temperature and the like. Examples of the (total) concentration of the nucleic acid binding protein(s) include, but not limited to, 0.1 mg/ml or more, 0.2 mg/ml or more, 0.3 mg/ml or more, 0.4 mg/ml or more, 0.5 mg/ml or more, 0.6 mg/ml or more, 0.7 mg/ml or more, 0.8 mg/ml or more, 0.9 mg/ml or more, 1.0 mg/ml or more, 1.5 mg/ml or more, 2.0 mg/ml or more, 2.5 mg/ml or more, 3.0 mg/ml or more, 3.5 mg/ml or more, 4.0 mg/ml or more, 4.5 mg/ml or more, 5.0 mg/ml or more, and 5.5 mg/ml or more. The upper limit of the (total) concentration of the nucleic acid binding protein(s) is not particularly limited, and examples thereof include 10.0 mg/ml or less, 9.0 mg/ml or less, 8.0 mg/ml or less, 7.0 mg/ml or less, and 6.0 mg/ml or less.

<Solution>

The solution containing a nucleic acid binding protein and an oligonucleotide (the solution of the present invention) is prepared by mixing the nucleic acid binding protein(s) and the oligonucleotide(s) in a solvent. Examples of the solvent in which the nucleic acid binding protein and the oligonucleotide are mixed include, but not limited to, water and a buffer.

The solution of the present invention may contain other ingredients in addition to the nucleic acid binding protein and the oligonucleotide. The composition of the solution of the present invention is not particularly limited as long as the effect of the present invention can be achieved, and it can be appropriately determined considering the type and concentration of the oligonucleotide, the type and concentration of the nucleic acid binding protein, the types and concentrations of other ingredients, the intended use, the storage temperature and the like.

The solution of the present invention preferably contains a buffer ingredient. In the present invention, the "buffer ingredient" refers to a compound or mixture having the ability to reduce the fluctuation of the hydrogen ion concentration (pH) in a solution. Preferable examples of the buffer ingredient contained in the solution of this invention include, but not limited to, Tris, Bicine, Tricine, HEPES, and phosphate (sodium phosphate, potassium phosphate, etc.). Particularly, Tris, Bicine, Tricine, HEPES, or phosphate is preferably used as the buffer ingredient in the present invention. For example, a TE buffer may be used as a solvent for mixing the nucleic acid binding protein and the oligonucleotide. The TE buffer is a standard solution used for dissolving and/or storing a nucleic acid, and functions to prevent nucleic acid degradation. The typical composition of TE buffer comprises 10 mM Tris-HCl (pH 7.2-8.0), and 1 mM EDTA.

The pH of the solution of the present invention is suitably adjusted within the range of, for example, pH 6.0 to pH 10.0, preferably pH 6.5 to pH 9.5, and more preferably pH 7.0 to pH 9.0. When the solution of the present invention is put in a PCR reaction solution, the type, concentration and pH of the buffer ingredient should be optimized in consideration of the reaction temperature, the DNA polymerase and other ingredients used.

The solution of the present invention may further contain an ingredient necessary or useful for amplifying a target nucleic acid, such as a deoxyribonucleotide, an enzyme (DNA polymerase, reverse transcriptase, etc.), a metal salt, a surfactant, or the like. Furthermore, the solution of the present invention may further contain an ingredient necessary or useful for detecting the amplified target nucleic acid, such as an intercalating dye or the like.

The deoxyribonucleotide contained in the solution of the present invention may be any deoxyribonucleotide that can be a substrate for an enzyme (DNA polymerase, reverse transcriptase, etc.). Examples of the deoxyribonucleotide include nucleotides having adenine, guanine, cytosine or thymine bases which are found in natural DNA, and mixtures thereof. In general, the DNA polymerase uses a deoxyribonucleotide having three phosphate moieties as a substrate for nucleic acid synthesis reaction. Accordingly, in one embodiment, the solution of the present invention contains a deoxyribonucleotide selected from the group consisting of deoxyribonucleoside triphosphates (e.g., dATP, dCTP, dITP, dGTP, and dTTP) and derivatives thereof. The deoxyribonucleotide derivatives include [aS] dATP, 7-deaza-dGTP, 7-deaza-dATP, and deoxynucleotide derivatives that are resistant to nucleolytic degradation. Examples of the nucleotide derivatives include deoxyribonucleotides labeled for detection with, for example, a radioisotope such as 32P or 35S, a fluorescent moiety, a chemiluminescent moiety, a bioluminescent moiety, or an enzyme.

The solution of the present invention may contain a DNA polymerase. When the solution of the present invention is used for PCR, the DNA polymerase contained in the solution of the present invention is preferably a thermostable DNA polymerase. Examples of DNA polymerases that can be used in the present invention include DNA polymerases derived from eubacteria such as bacteria belonging to genus *Thermus* or *Bacillus* (*Thermus aquaticus, Thermus thermophiles, Bacillus caldotenax*, etc.), archaea such as bacteria belonging to genus *Pyrococcus* or *Thermococcus* (*Pyrococcus furiosus, Thermococcus litalris, Thermococcus kodakaraensis*, etc.). Furthermore, mutants of the above-described DNA polymerases can also be used in the present invention.

Two or more DNA polymerases may be contained in the solution of the present invention. For example, a combination of a DNA polymerase having 3'→5' exonuclease activity and another DNA polymerase that does not have substantially exonuclease activity can be used in the present invention. A technique using such a combination of DNA polymerases is known as LA PCR (Long and Accurate PCR).

The solution of the present invention may contain reverse transcriptase. The reverse transcriptase contained in the solution of the present invention may be any reverse transcriptase that has reverse transcription activity, that is, the activity of synthesizing a DNA complementary to a template RNA. Examples of the reverse transcriptase include reverse transcriptases derived from viruses, such as Moloney murine leukemia virus (MMLV)-derived reverse transcriptase, and avian myeloblastosis virus (AMV)-derived reverse transcriptase, and variants thereof. Further examples of the reverse transcriptase include thermostable reverse transcriptases derived from eubacteria (DNA polymerases having reverse transcriptase activity), such as DNA polymerases derived from *Thermus* bacteria (e.g., *Thermus thermophilus*) and DNA polymerases derived from thermophilic *Bacillus* bacteria (e.g., *Bacillus caldotenax*).

The solution of the present invention may contain a metal salt. For example, a divalent metal ion salt essential for DNA polymerase activity may be used. Examples of the divalent metal ion include a magnesium ion, a manganese ion, and a cobalt ion. The divalent metal ion and its concentration suitable for each DNA polymerase are known in the art. The divalent metal ion may be supplied in the form of a salt such as chloride, sulfate, acetate or the like. Examples of the concentration of the divalent metal ion contained in the solution of the present invention include, but not limited to, 0.1 to 200 mM, preferably 0.2 to 100 mM, and more preferably 0.5 to 50 mM. The type and concentration of the salt should be optimized in accordance with the metal requirement of an enzyme (DNA polymerase, reverse transcriptase, etc.) to be used, a procedure for preparing a reaction solution containing the enzyme, and the like. The solution of the present invention may further contain other salts (sodium salt, potassium salt, ammonium salt, etc.).

The solution of the present invention may contain an intercalating dye. The intercalating dye to be contained in the solution of the present invention refers to a dye whose fluorescence is enhanced by intercalation into a double-stranded nucleic acid. The intercalating dye used in the present invention is preferably an intercalating dye that can be used in PCR. Examples of the intercalating dye include SYBR (registered trademark) Green I, TB Green (registered trademark), SYTO-60, SYTO-62, POPO-3, TOTO-3, BOBO-3, TO-PRO-3, YO-PRO-1, and SYTOX Orange, and among them, SYBR (registered trademark) Green I and TB Green (registered trademark) are preferred.

SYBR (registered trademark) Green I is a commercially available asymmetric cyanine dye, and its structure has been shown by Zipper H et al. ("Nucleic Acids Research", 2004, Vol. 32, No. 12, e103). According to Zipper H et al., the molar concentration of SYBR (registered trademark) Green I in a 10,000-fold diluted solution (1× concentration) of SYBR (registered trademark) Green I with DMSO which is available from Life Technologies is about 2 µM.

The solution of the present invention may contain a surfactant. Examples of the surfactant to be contained in the solution of the present invention include, but not limited to, nonionic surfactants such as Triton (registered trademark) X-100 (Polyoxyethylene (10) octylphenyl ether), Tween (registered trademark) 20 (Polyoxyethylene Sorbitan Monolaurate) and Nonidet (registered trademark) P-40 (Octylphenyl-polyethylene glycol); anionic surfactants such as poly(ethyleneglycol) 4-nonylphenyl 3-sulfopropyl ether (PNSE); cationic surfactants such as distearyl dimethyl ammonium chloride; and amphoteric surfactants such as cocamidopropyl betaine.

The concentration of the surfactant contained in the solution of the present invention is not particularly limited. When the solution of the present invention is used in PCR, the concentration of the surfactant contained in the solution of the present invention is adjusted so that the surfactant is contained at a suitable concentration in a PCR reaction solution to be prepared.

<Preparation>

A solution containing a nucleic acid binding protein and an oligonucleotide (the solution of the present invention) is prepared by mixing the nucleic acid binding protein and the oligonucleotide, and other ingredients as necessary, in a solvent. The preparation method is not particularly limited. It is preferable to prepare solutions in advance, each containing one of the ingredients at a high concentration, and put a necessary amount of each of the solutions in a container sequentially. The order of mixing the ingredients is not particularly limited as long as the effect of the present invention can be achieved. After all ingredients are put in the container, they are gently stirred and mixed until the all ingredients become homogenous. For example, stirring is performed by pipetting or inversion mixing.

<Storage>

The solution of the present invention thus prepared may be dispensed in containers and then stored. The material of the container used in the present invention is not particularly limited as long as the effect of the present invention can be achieved. At least, the container is preferably made of a material having low adsorptivity to oligonucleotides. The size and shape of the container used in the present invention are not particularly limited as long as the effect of the present invention can be achieved. The dispensing method and the dispensing amount are not particularly limited as long as the effect of the present invention can be achieved.

The solution prepared in the above-described step, that is, the "solution containing a nucleic acid binding protein and a nucleic acid (the solution of the present invention)" is stored at a low temperature.

In the present invention, the "low temperature" is not particularly limited as long as the effect of the present invention can be achieved. The low temperature can be appropriately determined in consideration of the type and concentration of the oligonucleotide, the type and concentration of the nucleic acid binding protein, and the mixing ratio of the oligonucleotide and the nucleic acid binding protein, the type and concentration of other ingredients, the storage time and the like. Examples of the low temperature include, but not limited to, 4° C. or lower, 0° C. or lower, −10° C. or lower, −20° C. or lower, −30° C. or lower, −40° C. or lower, −50° C. or lower, −60° C. or lower, −70° C. or lower, and −80° C. or lower. The temperature at which a solution is frozen is preferred.

The time for storing the solution of the present invention is not particularly limited as long as the effect of the present invention can be achieved, and can be appropriately determined in consideration of the type and concentration of the oligonucleotide, the type and concentration of the nucleic acid binding protein, and the mixing ratio of the oligonucleotide and the nucleic acid binding protein, the type and concentration of other ingredients, the storage temperature and the like. Examples of the storage time include, but not limited to, 24 hours or more, 2 days or more, 3 days or more, 4 days or more, 6 days or more, 1 week or more, 2 weeks or more, 3 weeks or more, 4 weeks or more, 5 weeks or more, 6 weeks or more, 7 weeks or more, and 8 weeks or more. The upper limit of the storage time is not particularly limited, and examples thereof include 10 years or less, 9 years or less, 8 years or less, 7 years or less, 6 years or less, 5 years or less, 4 years or less, 3 years or less, 2 years or less, 1 year or less, and the time until an expiration date. The expiration date may be appropriately determined in the range in which the solution of this invention can achieve the effect.

When the solution is stored in a frozen state, it can be melted by a suitable method and then used. The melting method is not particularly limited. For example, a container containing the frozen solution is left standing at room temperature, thereby the frozen solution can be melted. For example, a container containing the frozen solution is left standing in ice (or on ice) or in a thermostatic water bath, thereby the frozen solution can be melted.

An oligonucleotide stored by the oligonucleotide storage method of the present invention can be analyzed using a known nucleic acid analysis method. Examples of such a nucleic acid analysis method include a method for quantifying a nucleic acid and a method for analyzing an amplified product using nucleic acid amplification reaction such as PCR.

In an aspect of the present invention, an oligonucleotide stored by the oligonucleotide storage method of the present invention is used as a primer or a probe in a known nucleic acid analysis method. Examples of such a nucleic acid analysis method include synthesis of a complementary strand of a nucleic acid template (e.g., synthesis of cDNA), amplification of a target nucleic acid (e.g., PCR method), detection and quantification of a nucleic acid by various hybridization methods, and the like. The solution of the present invention containing a primer may contain a single primer, a pair of primers capable of amplifying a target nucleic acid, or a plural pairs of primers each of which corresponds to each of plural target nucleic acids. Similarly, the solution of the present invention containing a probe may contain one or more kinds of probes. Furthermore, in another aspect of the present invention, the solution of the present invention contains one or more primers and one or more probes.

An aspect of the present invention provides nucleic acid amplification reaction using the oligonucleotide contained in the solution of the present invention as a primer or as a probe. The nucleic acid amplification reaction is performed by mixing the solution of the present invention and various ingredients necessary for nucleic acid amplification reaction to prepare a reaction solution. The Ingredients necessary for nucleic acid amplification reaction are well known to a person skilled in the art. Typical examples of the ingredients include a DNA polymerase, a divalent metal ion, deoxyribonucleoside triphosphate, and a buffer ingredient. However, other ingredients can be also used as appropriate. When the oligonucleotide(s) contained in the solution of the present invention is/are a primer or a pair of primers, a suitable template nucleic acid or a sample possibly containing a template nucleic acid is added to the reaction solution. The nucleic acid amplification reaction can be used for qualitative detection and/or quantification of a template nucleic acid.

For DNA quantification using a monitoring result of nucleic acid amplification process, a method known in the art may be used. For example, a calibration curve is prepared by preparing a dilution series of standard DNA (positive control DNA) having a nucleotide sequence that is a template for nucleic acid amplification by a primer pair to be used for nucleic acid amplification reaction, and then performing real-time PCR using each dilution as a template to calculate a Ct value. Based on the calibration curve, a DNA in a sample can be quantified. As the standard DNA, for example, a plasmid DNA can be used. Examples of a method for calculating a Ct value include a method comprising evaluating an intersection of a threshold and an amplification curve as a Ct value (Crossing Point method), and a method comprising finding a second derivative of an amplification curve and evaluating the maximum point as a Ct value (2nd Derivative Maximum method).

The method may further comprise a step of performing melting curve analysis. In the melting curve analysis, the temperature of the reaction solution is gradually raised after the nucleic acid amplification reaction, and at the same time, a fluorescence signal from an intercalating dye is monitored. At a low temperature, the nucleic acid amplification product forms a double strand and shows a strong fluorescence signal. When a certain temperature is reached, the double strand is dissociated into single strands, and the fluorescence signal intensity from the intercalating dye rapidly decreases. At this time, the temperature is the melting temperature (Tm value). The Tm value of the amplification product may be examined by melting curve analysis to determine whether it is a specific amplification product.

A nucleic acid detection/quantification method using a labeled probe is known. A typical example of the method comprises bringing a probe double-labeled with a fluorescent substance and a quenching substance into contact with a target nucleic acid so that the probe is cleaved when the probe and the target nucleic acid are hybridized. The target nucleic acid can be detected and/or quantified based on the fluorescence generated when the probe is cleaved. Examples of such a method include a Taqman method which comprises cleaving a probe by a DNA polymerase having 5'→3' exonuclease activity, and a cycling probe method which comprises cleaving a DNA/RNA chimeric probe by ribonuclease H. The solution of the present invention may contain a labeled probe (oligonucleotide) that can be used for purposes as described above.

As one embodiment, the solution of the present invention containing a primer pair to be used for amplification of a target nucleic acid and a nucleic acid binding protein may further contain an ingredient (other than a template nucleic acid) necessary for nucleic acid amplification reaction (premix solution). To such a solution, a template nucleic acid or a sample possibly containing the template nucleic acid is added, and thereby a reaction solution for nucleic acid amplification can be easily prepared, which is useful for rapid detection and quantification of the template nucleic acid. Since the efficiency of the nucleic acid amplification reaction does not decrease even after the solution is stored for a long time, detection and quantification can be performed with good reproducibility.

(2) "Kit for Amplifying a Target Nucleic Acid" of the Present Invention

As an embodiment, the solution of the present invention containing a nucleic acid binding protein and an oligonucleotide that hybridizes to a target nucleic acid is useful for detection or amplification of the target nucleic acid. When the solution of the present invention is stored at a low temperature, the degradation of the oligonucleotide is further suppressed. Thus, the detection and quantification of the target nucleic acid can be performed with good reproducibility by preferably using the solution of the present invention stored at a low temperature. Examples of the oligonucleotide include an oligonucleotide that functions as a probe for detecting a target nucleic acid, and an oligonucleotide that functions as a primer in amplification of a target nucleic acid. Accordingly, in an aspect of the present invention, a kit for amplifying a target nucleic acid which comprises a solution containing a nucleic acid binding protein and an oligonucleotide that hybridizes to the target nucleic acid (hereinafter, referred to as "the kit of the present invention") is provided.

The kit of the present invention may further comprise various ingredients necessary or useful for nucleic acid amplification, for example, the above-described enzyme (e.g., DNA polymerase, reverse transcriptase, etc.), metal salt (e.g., divalent metal ion), deoxyribonucleotide (e.g., deoxyribonucleoside triphosphate), buffer ingredient, surfactant, and the like. These ingredients may be, for example, one or more ingredients selected from the group consisting of a DNA polymerase, a divalent metal ion, deoxyribonucleoside triphosphate, and a buffer ingredient. Each of the ingredients necessary or useful for nucleic acid amplification may be comprised in the kit as a separate component, or two or more of the ingredients necessary or useful for nucleic acid amplification may be comprised in the kit as one component. Furthermore, the solution containing a nucleic acid binding protein and an oligonucleotide that hybridizes to a target nucleic acid may contain one or more of these ingredients.

As an aspect of the kit of the present invention, a kit comprising a combination of a solution containing a nucleic acid binding protein and an oligonucleotide that hybridizes to a target nucleic acid, and a solution containing a DNA polymerase is useful for amplification and detection of the target nucleic acid. When the oligonucleotide that hybridizes to a target nucleic acid is a primer, both of the solutions can be mixed to prepare a reaction solution for amplification of the target nucleic acid. When the oligonucleotide that hybridizes to a target nucleic acid is a probe, a suitable primer as well as both of the solutions can be used to prepare a reaction solution for amplification of the target nucleic acid. The solution containing a nucleic acid binding protein and an oligonucleotide that hybridizes to a target nucleic acid, or the solution containing a DNA polymerase may further contain one or more the ingredients necessary or useful for nucleic acid amplification as described above. For example, the kit may comprise a first solution containing a nucleic acid binding protein and an oligonucleotide that hybridizes to a target nucleic acid, and a second solution containing one or more elements selected from the group consisting of a DNA polymerase, a divalent metal ion, deoxyribonucleoside triphosphate, and a buffer ingredient. Each of the components as described above is stored in a separate container, or the first solution and the second solution are stored in separate containers.

An example of another aspect of the kit of the present invention is a kit comprising, as a component(s), a solution (premix solution) containing all of ingredients necessary for nucleic acid amplification reaction and other ingredients (other than a template nucleic acid) as well as an oligonucleotide that hybridizes to a target nucleic acid and a nucleic acid binding protein. An example of the premix solution is a solution containing a DNA polymerase, a divalent metal ion, deoxyribonucleoside triphosphate and a buffer ingredient as well as a nucleic acid binding protein and an oligonucleotide that hybridizes to a target nucleic acid. This kit is useful for rapid detection and quantification of a template nucleic acid, because a reaction solution for nucleic acid amplification can be easily prepared by adding a template nucleic acid or a sample possibly containing the template nucleic acid to the component(s) of the kit. Since the efficiency of the nucleic acid amplification reaction does not decrease even after the kit is stored for a long time, the detection and quantification can be performed with good reproducibility.

In a preferred aspect of the present invention, the kit of the present invention may contain a positive control nucleic acid having at least a part of the nucleotide sequence of a target nucleic acid, a reagent for used in sample pretreatment, and the like.

Another aspect of the present invention provides use of a nucleic acid binding protein for stably storing an oligonucleotide. According to this aspect, a decrease in the efficiency of nucleic acid amplification is prevented in nucleic acid amplification reaction by using a reaction solution containing the stored oligonucleotide. Specifically, the "use of a nucleic acid binding protein" of the present invention can be performed as described in the "oligonucleotide storage method" of the present invention, and is useful for a target nucleic acid amplification/detection method, and production of a kit to be used in the method.

The kit of the present invention is preferably stored at a low temperature until use. Particularly preferably, in the kit of the present invention, the solution containing a nucleic acid binding protein and an oligonucleotide that hybridizes to a target nucleic acid is stored at a low temperature. Although the present invention is not particularly limited, the solution containing a nucleic acid binding protein and an oligonucleotide that hybridizes to a target nucleic acid is desirably stored in a frozen state.

EXAMPLES

The present invention is further specifically explained by the following examples, to which the scope of the present invention is not limited.

Preparation Example 1

Preparation of CspA Stock Solution

According to a method described in S. Chatterjee et al. (J. Biochem., 1993, 114, 663-669), *E. coli* CspA protein was expressed and purified, and then, a CspA stock solution [10 mg/mL CspA protein, 20 mM Tris-HCl (pH 7.8 (4° C.)), 100 mM NaCl, 1 mM EDTA, 1 mM DTT, 50% Glycerol] was prepared. The CspA stock solution was dispensed into tubes and stored in a frozen state at −20° C. until use.

Preparation Example 2

Preparation of Primer Stock Solution

Each of InvA_F-6 primer (SEQ ID NO: 1), invA_R-6 primer (SEQ ID NO: 2), and stx1_R-2 primer (SEQ ID NO: 3) was dissolved in a TE buffer (pH 8.0). Primer stock solutions (100 µM) were prepared. The primer stock solution was dispensed into tubes and stored in a frozen state at −20° C. until use.

Example 1

Decrease Over Time in PCR Reactivity of Primer Mix Solution

The primer stock solutions and a TE buffer were mixed to prepare a primer mix solution. The prepared primer mix solution contained invA_F-6 primer (10 µM, SEQ ID NO: 1), invA_R-6 primer (10 µM, SEQ ID NO: 2), and stx1_R-2 primer (10 µM, SEQ ID NO: 3) in the TE buffer.

The primer mix solution was dispensed into tubes and stored in a frozen state at −20° C. Before freezing, the primer mix solution was subjected to PCR, and 3, 5, 7 and 10 days after starting to freeze the primer mix solution, the frozen primer mix solution was thawed and subjected to PCR. Regarding the primer mix solution before freezing, it was subjected to PCR immediately after preparation. Regarding the cryopreserved primer mix solution, it was subjected to PCR quickly after it was thawed. In the following Examples, PCR was performed in the same manner.

A PCR reaction solution (n=2) was prepared. Specifically, 2.5 µl of the primer mix solution, 12.5 µl of Reaction Mix Fast included in TaKaRa intestinal pathogenic bacteria gene detection kit (RR139A, manufactured by Takara Bio Inc.), 0.25 µl of 100×SYBR (registered trademark) Green I (manufactured by Takara Bio Inc.) and sterile water were mixed so as to be a final volume of 25 µl. PCR and fluorescence detection were performed with Thermal Cycler Dice (registered trademark) Real Time System III (TP950, manufactured by Takara Bio Inc.). PCR was performed according to the following reaction conditions: pre-heating at 94° C. for 30 seconds, and then 45-cycle reaction in which each cycle consists of 90° C. for 1 second and 64° C. for 10 seconds. Finally, dissociation reaction involving temperature raise from 68° C. to 90° C. over time was performed to observe fluorescence intensity at each temperature point. As a control, the same measurement was performed using a reaction solution containing 5 pg of Salmonella genome as a template DNA.

As examples, an amplification curve and a melting curve obtained when the primer mix solution before freezing was subjected to PCR as described above are shown in FIG. 1 and FIG. 2, respectively. As shown in FIG. 1, when the reaction solution containing the template DNA (control) was used, the fluorescence rose faster as compared with the case where the reaction solution containing no template DNA was used. In FIG. 2, a peak near 85° C. is derived from an amplification product of an invA gene fragment, and peaks near 73° C. are derived from a non-specific amplification product. These results show that a non-specific amplification product formed when the reaction solution containing no template DNA was used. In other words, the formation of a non-specific amplification product can be monitored by analyzing an amplification curve and a melting curve.

Based on the measurement results, changes over time in a Ct value obtained using the reaction solution containing no template DNA are calculated, and shown in FIG. 3. As shown in FIG. 3, when the cryopreserved primer mix solution was used, the Ct value decreased over time in spite of the fact that the reaction solution did not contain a template DNA. This result shows that non-specific amplification products tend to form as the storage period of a primer mix solution becomes longer.

Example 2

PCR Reactivity Maintenance by Addition of CspA to Primer Mix Solution

A primer mix solution containing three kinds of primers and an additive (CspA or Tween 20) was prepared. Specifically, the primer mix solution containing CspA was prepared in the same manner as in Example 1, except that a CspA protein (manufactured by Takara Bio Inc.) was further added at a final concentration of 4 mg/ml. The primer mix solution containing Tween 20 was prepared in the same manner as in Example 1, except that Tween (registered trademark) 20 (manufactured by Nacalai Tesque) was added at a final concentration of 0.5%. As a control, a primer mix solution containing no additive was prepared and used as a TE control.

These primer mix solutions were dispensed into tubes and stored in a frozen state at −20° C. Before freezing, the primer mix solutions were subjected to PCR, and 3 and 6 days after starting to freeze the primer mix solutions, the frozen primer mix solutions were thawed and subjected to PCR. A PCR reaction solution (n=4) was prepared by the same method as described in Example 1, and PCR was performed under the conditions described in Example 1. In order to bring the PCR conditions in line, when the TE control and the Tween 20-containing primer mix solution were used to prepare PCR reaction solutions, a CspA protein was added to the PCR reaction solutions. Based on the measurement results, Ct values obtained using the reaction solutions containing no template DNA are calculated, and shown in FIG. 4.

As shown in FIG. 4, the decrease in the Ct value was suppressed by adding CspA or Tween 20 to the primer mix solution. Particularly, the decrease in Ct value was effectively suppressed by adding CspA. This result shows that the formation of non-specific amplification products can be suppressed by storing a primer mix solution with addition of CspA.

Example 3

Evaluation of CspA Concentration (First Time)

Primer mix solutions containing three kinds of primers and CspA at different concentrations were prepared. Specifically, the primer mix solutions containing CspA at different concentrations were prepared in the same manner as in Example 1, except that a CspA protein was further added at a final concentration of 4 mg/ml or at a final concentration of 2 mg/ml. As a control, a primer mix solution not containing CspA was prepared and used as a TE control.

These primer mix solutions were dispensed into tubes and stored in a frozen state at −20° C. Before freezing, the primer mix solutions were subjected to PCR, and 3 and 6 days after starting to freeze the primer mix solutions, the frozen primer mix solutions were thawed and subjected to PCR. A PCR reaction solution (n=4) was prepared by the same method as described in Example 1, and PCR was performed under the conditions described in Example 1. In order to bring the PCR conditions in line, when the TE control and the primer mix solution containing 2 mg/ml CspA were used to prepare PCR reaction solutions, a CspA protein was added to the PCR reaction solutions. Based on the measurement results, Ct values obtained using the reaction solutions containing no template DNA are calculated, and shown in FIG. 5.

As shown in FIG. 5, when the primer mix solution containing CspA at a final concentration of 4 mg/ml or 2 mg/ml was used, the decrease in Ct value was suppressed as compared to the case where the primer mix solution not containing CspA (TE control) was used. This result shows that the formation of non-specific amplification products can be suppressed by storing a primer mix solution with addition of CspA at a final concentration of 4 mg/ml or a final concentration of 2 mg/ml.

Example 4

Evaluation of CspA Concentration (Second Time)

Primer mix solutions containing three kinds of primers and CspA at different concentrations were prepared. Specifically, the primer mix solutions containing CspA at different concentrations were prepared in the same manner as in Example 1, except that a CspA protein was further added at a final concentration of 4 mg/ml, at a final concentration of 1 mg/ml, or a final concentration of 0.25 mg/ml. As a control, a primer mix solution not containing CspA was prepared and used as a TE control.

These primer mix solutions were dispensed into tubes and stored in a frozen state at −20° C. Before freezing, the primer mix solutions were subjected to PCR, and 3 and 7 days after starting to freeze the primer mix solutions, the frozen primer mix solutions were thawed and subjected to PCR. A PCR reaction solution (n=4) was prepared by the same method as described in Example 1, and PCR was performed under the conditions described in Example 1. In order to bring the PCR conditions in line, when the TE control, the primer mix solution containing 1 mg/ml CspA, and the primer mix solution containing 0.25 mg/ml CspA were used to prepare PCR reaction solutions, a CspA protein was added to the PCR reaction solutions. Based on the measurement results, Ct values obtained using the reaction solutions containing no template DNA are calculated, and shown in FIG. 6.

As shown in FIG. 6, the Ct value decreased depending on the concentration of CspA. This result shows that the formation of non-specific amplification products can be suppressed depending on the concentration of CspA added to a primer mix solution.

Example 5

PCR Reactivity Maintenance by Addition of Nucleic Acid-Binding Protein to Primer Mix Solution A primer mix solution containing three kinds of primers and a nucleic acid-binding protein (CspA, T4 SSB, or E. coli SSB) was prepared. Specifically, when a TE buffer containing invA_F-6 primer (20 μM, SEQ ID NO: 1), invA_R-6 primer (20 μM, SEQ ID NO: 2), and stx1_R-2 primer (20 μM, SEQ ID NO: 3) was prepared, a CspA protein (final concentration: 4 mg/ml), a T4 phage-derived SSB protein (final concentration: 2 mg/ml, manufactured by Bio Academia) or an E. coli SSB protein (final concentration: 2 mg/ml, manufactured by Bio Academia) was further added to prepare the primer mix solution containing a nucleic acid-binding protein. As a control, a primer mix solution containing no nucleic acid-binding protein was prepared and used as a TE control.

These primer mix solutions were dispensed into tubes and stored in a frozen state at −20° C. Before freezing, the primer mix solutions were subjected to PCR, and 2, 5 and 9 days after starting to freeze the primer mix solutions, the frozen primer mix solutions were thawed and subjected to PCR.

A PCR reaction solution (n=4) was prepared. Specifically, 1.25 μl of the primer mix solution, 12.5 μl of Reaction Mix Fast, 0.25 μl of 100×SYBR (registered trademark) Green I, and sterile water were mixed so as to be a final volume of 25 μl. PCR was performed under the conditions described in Example 1. In order to bring the PCR conditions in line, when the TE control was used to prepare a PCR reaction solution, a CspA protein was added to the PCR reaction solution. Based on the measurement results, Ct values (ratios) obtained using the reaction solutions containing no template DNA are calculated, and shown in FIG. 7.

As shown in FIG. 7, the decrease in the Ct value was suppressed by adding the nucleic acid binding protein (CspA, T4 SSB, or E. coli SSB) to the primer mix solution. This result shows that the formation of non-specific amplification products can be suppressed by storing a primer mix solution with addition of a nucleic acid binding protein.

Example 6

PCR Reactivity Maintenance by Addition of CspA to Premix Solution

A premix solution containing ingredients necessary for PCR (primer, dNTP, enzyme, fluorescent dye, etc.) other than a template DNA, and CspA was prepared. Specifically, the prepared premix solution contained, per 14.5 μl volume, invA_F-6 primer (1.7 μM, SEQ ID NO: 1), invA_R-6 primer (1.7 μM, SEQ ID NO: 2), stx1R-2 primer (1.7 μM, SEQ ID NO: 3), Reaction Mix Fast (12.5 μl), SYBR (registered trademark) Green I (1.7×), and CspA (0.69 mg/ml). As a control, a premix solution not containing CspA was prepared and used as a TE control.

These premix solutions were dispensed into tubes and stored in a frozen state at −20° C. Before freezing, the premix solutions were subjected to PCR, and 3 and 7 days after starting to freeze the premix solutions, the frozen premix solutions were thawed and subjected to PCR. Specifically, 14.5 μl of the premix solution and 10.5 μl of sterile water were mixed to prepare a PCR reaction solution, and PCR was performed under the conditions described in Example 1 (n=4). Based on the measurement results, Ct values obtained using the reaction solutions containing no template DNA are calculated, and shown in FIG. 8.

As shown in FIG. 8, the decrease in the Ct value was suppressed by adding CspA to the premix solution. This result shows that the formation of non-specific amplification products can be suppressed by storing a premix solution with addition of CspA.

INDUSTRIAL APPLICABILITY

The present invention is useful in a wide range of fields including genetic engineering, biology, medicine and agriculture.

Sequence Listing Free Text
SEQ ID NO: 1; PCR primer "invAF_6"
SEQ ID NO: 2; PCR primer "invAR_6"
SEQ ID NO: 3; PCR primer "stx1_R-2"

The invention claimed is:

1. A method for storing an isolated oligonucleotide, the method comprising a step of storing a solution containing a nucleic acid binding protein and an isolated oligonucleotide in a frozen state, wherein the nucleic acid binding protein is a protein selected from the group consisting of cold shock proteins and single-stranded binding protein (SSB).

2. The method according to claim 1, wherein the nucleic acid binding protein is a protein selected from the group consisting of CspA, T4 phage-derived SSB, and E. coli-derived SSB.

3. The method according to claim 1, wherein the isolated oligonucleotide is an isolated oligodeoxyribonucleotide.

4. A kit for amplifying a target nucleic acid, comprising a solution containing a nucleic acid binding protein and an oligonucleotide that hybridizes to the target nucleic acid, wherein the solution is a frozen solution.

5. The kit according to claim 4, wherein the nucleic acid binding protein is a protein that binds to a single-stranded nucleic acid.

6. The kit according to claim 5, wherein the protein that binds to a single-stranded nucleic acid is a protein selected from the group consisting of cold shock proteins and SSB.

7. The kit according to claim 6, wherein the protein that binds to a single-stranded nucleic acid is a protein selected from the group consisting of CspA, T4 phage-derived SSB, and E. coli-derived SSB.

8. The kit according to claim 4, wherein the oligonucleotide is an oligodeoxyribonucleotide.

9. The kit according to claim 8, wherein the oligodeoxyribonucleotide is a primer used for amplification of the target nucleic acid.

10. The kit according to claim 4, comprising a first solution containing a nucleic acid binding protein and an oligonucleotide that hybridizes to the target nucleic acid, and a second solution containing one or more elements selected from the group consisting of a DNA polymerase, a divalent metal ion, deoxyribonucleoside triphosphate, and a buffer ingredient.

11. The kit according to claim 4, wherein the solution containing a nucleic acid binding protein and an oligonucleotide that hybridizes to the target nucleic acid further contains a DNA polymerase, a divalent metal ion, deoxyribonucleoside triphosphate, and a buffer ingredient.

12. The method according to claim 1, wherein the formation of non-specific amplification products in a nucleic acid amplification reaction is suppressed when the oligonucleotide stored in the solution containing a nucleic acid binding protein in a frozen state is used in the nucleic acid amplification reaction.

13. A method for amplifying a nucleic acid, the method comprising using an oligonucleotide in a solution containing a nucleic acid binding protein stored by the method according to claim 1, wherein the formation of non-specific amplification products is suppressed in the nucleic acid amplification reaction.

14. The method according to claim 2, wherein the nucleic acid binding protein is CspA.

15. The kit according to claim 7, wherein the protein that binds to a single-stranded nucleic acid is CspA.

* * * * *

SEQUENCE LISTING

<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: PCR primer "invA_F-6"

<400> SEQUENCE: 1
ggcaattcgt tattggcgat ag                                            22

<210> SEQ ID NO 2
<211> LENGTH: 20
<212> TYPE: DNA
<213> ORGANISM: Artificial Sequence
<220> FEATURE:
<223> OTHER INFORMATION: PCR primer "invA_R-6"

```
<400> SEQUENCE: 2
taccgggcat accatccaga                                             20

<210> SEQ ID NO 3
<211> LENGTH: 23
<212> TYPE: DNA
<213> ORGANISM: Artificial Sequence
<220> FEATURE:
<223> OTHER INFORMATION: PCR primer "stx1_R-2"

<400> SEQUENCE: 3
tcgttgacta cttcttatct gga                                         23
```